United States Patent
Jensen et al.

(10) Patent No.: US 9,329,121 B2
(45) Date of Patent: May 3, 2016

(54) SENSOR UTILIZING BAND PASS FILTERS

(75) Inventors: Jens Moeller Jensen, Horsens (DK); Arun Krishna, Tilst (DK); Lars Munch, Vamdrup (DK); Rainer Buchner, Boerkop (DK); Thomine Stolberg-Rohr, Vejle (DK); Henrik Gedde Moos, Fredericia (DK)

(73) Assignee: Danfoss IXA A/S, Vejle (DK)

( * ) Notice: Subject to any disclaimer, the term of this patent is extended or adjusted under 35 U.S.C. 154(b) by 845 days.

(21) Appl. No.: 13/264,419

(22) PCT Filed: Apr. 16, 2010

(86) PCT No.: PCT/DK2010/000045
§ 371 (c)(1),
(2), (4) Date: Dec. 22, 2011

(87) PCT Pub. No.: WO2010/118748
PCT Pub. Date: Oct. 21, 2010

(65) Prior Publication Data
US 2012/0090379 A1    Apr. 19, 2012

(30) Foreign Application Priority Data

Apr. 17, 2009   (DK) ................................ 2009 00506

(51) Int. Cl.
| | |
|---|---|
| *G01J 1/00* | (2006.01) |
| *G01J 1/10* | (2006.01) |
| *G01J 5/02* | (2006.01) |
| *G01J 5/10* | (2006.01) |
| *G01N 21/3504* | (2014.01) |
| *G01J 3/02* | (2006.01) |
| *G01J 3/36* | (2006.01) |
| *G01N 21/31* | (2006.01) |
| *G01J 3/427* | (2006.01) |
| *G01J 3/12* | (2006.01) |

(52) U.S. Cl.
CPC ............ *G01N 21/3504* (2013.01); *G01J 3/02* (2013.01); *G01J 3/027* (2013.01); *G01J 3/36* (2013.01);
(Continued)

(58) Field of Classification Search
CPC ............ G01N 2021/3522; G01N 2021/3188; G01N 2021/3185; G01N 2021/3177; G01N 2021/3166; G01N 21/314; G01J 3/427; G01J 1/00; G01J 1/10; G01J 5/10; G01J 5/02
USPC ................................ 250/338.1, 339.01, 336.1
See application file for complete search history.

(56) References Cited

U.S. PATENT DOCUMENTS

| | | | |
|---|---|---|---|
| 5,081,998 A | 1/1992 | Yelderman et al. | |
| 5,650,624 A | 7/1997 | Wong | |

(Continued)

FOREIGN PATENT DOCUMENTS

| | | |
|---|---|---|
| CN | 1216108 A | 5/1999 |
| CN | 101363796 A | 2/2009 |

(Continued)

OTHER PUBLICATIONS

International Search Report for Serial No. PCT/DK2010/000045 dated Jul. 2, 2010.

*Primary Examiner* — David Porta
*Assistant Examiner* — Carolyn Igyarto
(74) *Attorney, Agent, or Firm* — McCormick, Paulding & Huber LLP (57) ABSTRACT

The invention relates to a sensor having a filter arrangement, downstream of which there is arranged a detector arrangement, and an evaluating device connected to the detector arrangement. The filter arrangement has at least a first filter, the suspect filter, and at least one second filter, the reference filter(s). The first filter is configured as a band pass filter allowing the passage of a first predetermined band, the suspect band. The at least one second filter is configured as a band pass filter allowing the passage of a second predetermined band(s), the reference band(s). The detector arrangement has at least one detector associated with at least one of the filters. The band passes reference filters are distributed above and below the band pass of the suspect filter. The sensor with advantage could be utilized within the IR band, and could advantageously be used to detect CO2.

10 Claims, 9 Drawing Sheets

(52) U.S. Cl.
CPC ............. *G01N 21/314* (2013.01); *G01J 1/00* (2013.01); *G01J 1/10* (2013.01); *G01J 3/427* (2013.01); *G01J 5/02* (2013.01); *G01J 5/10* (2013.01); *G01J 2003/1213* (2013.01)

(56) References Cited

U.S. PATENT DOCUMENTS

| | | |
|---|---|---|
| 5,672,874 A | 9/1997 | Fujii et al. |
| 5,721,430 A | 2/1998 | Wong |
| 5,995,008 A | 11/1999 | King et al. |
| 2002/0011568 A1 | 1/2002 | Diekmann |
| 2003/0102434 A1 | 6/2003 | Nakauchi et al. |
| 2003/0147080 A1 | 8/2003 | Sarkis et al. |
| 2008/0283753 A1 | 11/2008 | Jensen et al. |

FOREIGN PATENT DOCUMENTS

| | | |
|---|---|---|
| DE | 19835335 C1 | 11/1999 |
| JP | 2003014639 A | 1/2003 |
| JP | 2005221416 A | 8/2005 |
| JP | 2005257358 A | 9/2005 |
| JP | 2006038721 A | 2/2006 |
| WO | 2004113887 A2 | 12/2004 |

SENSOR UTILIZING BAND PASS FILTERS

CROSS REFERENCE TO RELATED APPLICATIONS

This application is entitled to the benefit of and incorporates by reference essential subject matter disclosed in International Patent Application No. PCT/DK2010/000045 filed on Apr. 16, 2010 and Danish Patent Application No. PA 2009 00506 filed Apr. 17, 2009.

FIELD OF THE INVENTION

The invention relates to a sensor having a filter arrangement, downstream of which there is arranged a detector arrangement, and an evaluating device which is connected to the detector arrangement, the filter arrangement has at least a first filter, the suspect filter, which is configured as a band pass filter allowing the passage of a first predetermined band, the suspect band, at least one second filter, the reference filter(s), which is configured as a band pass filter allowing the passage of a second predetermined band(s), the reference band(s), and where the detector arrangement has at least one detector associated with at least one of the filters. The band passes reference filters are distributed above and below the band pass of the suspect filter. The sensor with advantage could be utilized within the IR band, and could advantageously be used to detect $CO_2$.

BACKGROUND OF THE INVENTION

Such a sensor, which is configured as a gas sensor, is known, for example, from U.S. Pat. No. 5,081,998 A. An IR radiation source is provided therein, which acts upon a total of four detectors by way of a filter arrangement. The filter arrangement has two filters having different pass characteristics. A first filter has a pass band for IR radiation that is absorbed by $CO_2$. That filter is therefore also referred to as a "$CO_2$ filter". The detectors arranged downstream are designated $CO_2$ detectors. The other filter has a pass band different therefrom which serves for determining a reference quantity. The detectors arranged downstream of that reference filter are referred to as reference detectors. Between the IR source and the two filters there is arranged a third filter which is referred to as a natural density filter and overlaps half of the first filter and half of the second filter. Accordingly, one of the two $CO_2$ detectors and one of the reference detectors receives only IR radiation that has passed both through the natural density filter and through either the $CO_2$ filter or the reference filter. In the evaluating device, the difference of the output signals of the two $CO_2$ detectors and the difference of the two reference detectors is formed. The two differences are then divided by one another. Such a $CO_2$ sensor is required, for example, for determining $CO_2$ in a patient's breath so as to be better able to monitor the patient during anaesthesia.

A disadvantage of such sensors is that they have a relatively high power requirement, and another disadvantage is the number of detectors required. The arrangement known from U.S. Pat. No. 5,081,998 A requires a source of radiation which, in any case for prolonged use, makes it unsuitable for battery-operated use. Furthermore, such an IR source generally requires a certain heating-up period, so that without a degree of prior preparation it is not always possible to carry out measurements when desired.

The problem underlying the invention is to simplify the use of an IR sensor, which is introduced in the sensor described in US 2008/0283753, wherein the pass band of a first filter is arranged within the pass band of a second filter and the evaluating device forms the difference of the signals of the detectors and normalizes it to the signal of a detector.

That configuration makes it possible to evaluate substantially more IR radiation. The IR radiation is therefore not divided into two separate ranges, with each detector detecting only one range. Instead, one detector detects IR radiation having a pre-set spectral range, which also includes, for example, the absorption spectrum of the gas being determined, here $CO_2$. The other detector detects an IR spectrum from a sub-range thereof, which does not include the absorption spectrum of the gas being determined. The normalization of the difference to the output signal of a detector enables fluctuations in the intensity of the IR radiation to be compensated. It is also possible to use more than two sensors with a correspondingly greater number of filters, the individual pass ranges then overlapping accordingly. With such a sensor it is also possible to obtain other information, for example relating to temperature, to movement in the room, to the number of persons in the room, etc. Because it is possible to detect substantially more radiation, the power consumption can be reduced, so that the necessary power can also be supplied by a battery. That in turn gives greater freedom in terms of local mounting and use. The sensor can transmit its signals wirelessly.

The pass band of the first filter is preferably larger than the pass band of the second filter. Accordingly, the first filter, in addition to including the spectral range allowed to pass by the second filter, also includes the spectral range in which IR radiation is absorbed.

The two filters preferably have a common cut-off wavelength. That simplifies evaluation. The difference between the output signals of the detectors can then readily be formed without additional calculation steps being necessary. The cut-off wavelengths are the wavelengths that define, that is to say limit, the pass bands. They are referred to as "lower wavelength" and "upper wavelength".

It is how ever a known situation, that the amount as well as the spectral distribution of radiation of an emitter has a dependence of the temperature of the emitter. This is given by the well known Planck's distribution of radiation. Given a temperature of the emitter, a Planck curve then gives the dependence of the radiation to the wavelength, where the Planck curves has a maximum radiation at some wavelength, the maximum radiation value as well as the wavelength of the maximum radiation being temperature dependent.

Using a natural source in sensor systems such like the one described in for example US 2008/0283753, would make the pass bands of the filters change in energy (or in other words, the radiation intensity density) over the band of wavelengths.

This construction is able to compensate for changes in the intensity of radiation of the light source, however, is not robust to for example temperature changes of the light source.

It is one object of the present invention to introduce methods to solve these problems of the present sensors, and a sensor utilizing the solutions.

SUMMARY OF THE INVENTION

The present invention solves these problems by introducing that the suspect filter and the reference filter(s) has different cut-off wavelengths, in that both the both lower wavelengths and upper wavelengths differs. The "lower wavelength" is the lowest wavelength from which the filters allow passage of radiation, and the "upper wavelength" is the highest wavelength higher that the lower wavelength, from which the filters shuts off passage of radiation.

The ranges of allowed wavelengths of the suspect filter are in the following being referred to as the "suspect band", and the allowed wavelengths of the reference filter(s) are in the following being referred to as the "reference band(s)".

As written, the suspect lower wavelength in the present invention is different to the reference lower length(s), and the suspect upper wavelength is different to the reference upper wavelength(s). This has the advantage that changes, such like the spectral distribution of the intensity of the incoming radiation, for example caused by temperature fluctuations of the source, can be compensated by distributing the reference band(s) above and below the suspect band. In one preferred embodiment of the present invention, this distribution is so that by a change in temperature, the increase in radiation intensity (or intensity density or energy) over the reference band roughly equals the increase in radiation intensity (or intensity density or energy) over the suspect band.

In one alternative or additional embodiment, the mean value, or average, of the radiation intensity density (or energy) over the suspect band roughly equals the mean value, or average, of the radiation intensity density (or energy) over each of the reference bands.

In one alternative or additional embodiment, the radiation intensity density (or energy) over the suspect band roughly equals the mean value, or average, of the radiation intensity density (or energy) over the whole of the combined reference bands. (the 'reference filter system band' is the combined reference bands of all the reference filters).

In another alternative or additional embodiment, the radiation intensity density (or energy) over the suspect band roughly equals the mean value, or average, of the radiation intensity density (or energy) of one of or each of the reference bands.

The filters of the present invention may be formed by filter elements in series, or by one single filter element operating both as suspect filter and reference filter(s). When two or more filters are arranged as filter elements in series, they are arranged one after the other in the radiation direction, that is to say between the radiation source(s) and the detectors.

The sensor with advantage may operate within any radiation wavelength, and the source may be any radiation source.

The example in the following describes a sensor for determining the $CO_2$ content in an environment where a IR source would be preferred as light source, however, any other substances than $CO_2$ would also apply to the present invention, just as any other light source than within the IR band would apply.

In a further embodiment of the present invention, at least one reference filter (to be called the first reference filter) has a reference band, called the first reference band, with a wider span of wavelengths than the suspect band, where the first reference lower wavelength of this first reference filter is at a lower wavelength than the suspect lower wavelength, and the first reference upper wavelength of this first reference filter has a higher wavelength than the suspect upper wavelength. In this manner, the suspect band overlaps the first reference band.

In this embodiment, the centre wavelength of the first reference band (the first centre reference wavelength) and the centre wavelength of the suspect band may be the same, or may be different.

For a change in temperature, the relative change in intensity in the suspect and reference band must be equal in order for the temperature dependency to cancel out.

When using radiation sources, actively powered or natural the relative change in intensity depends unlinearly on the wavelengths spanned by the bands. Therefore the unmatching centre wavelength can be introduced to improve stability to temperature drift.

In this example, the reference filter(s) advantageously has a pass band that is from 0.2 to 1 μm greater than the pass band of the suspect filter. It is desirable for the suspect filter to cover basically only a relatively narrow wavelength range or spectral range of the radiation spectrum, for example the range in which IR radiation is absorbed by $CO_2$. The range indicated is sufficient for this. The risk that absorption by other gases will have an adverse effect on the measurement result and falsify that result is kept small.

It is preferable here for the first reference filter to have a pass band in the range from 4 to 4.5 μm and the suspect filter to have a pass band in the range from 4.1 to 4.4 μm. In dependence upon the gases or other quantities being detected, those spectral ranges can of course also be shifted.

In another preferred embodiment of the present invention, the system comprises a first and a second reference filter with a first and second reference band respectively (together constituting the combined reference bands), where the first and second reference bands are non-overlapping, meaning they span no common wavelengths. This may be an advantage if there are other gasses etc. in the environment than the gas(ses) of interest, with absorption bands in the vicinity of the suspect band, that could influence the measurements, in that it is difficult to avoid overlapping a reference band with such 'pollution' bands. By ensuring that at most one references band is affected by such a 'polluting' absorption band, it will be known that at least the other is unaffected.

In one preferred version of this embodiment, at least one of the first or second reference bands overlaps the suspect band, meaning that the first reference upper wavelength is at a higher wavelength than the suspect lower wavelength, and/or the second reference lower wavelength is at a lower wavelength than the suspect upper wavelength, but at a higher than the first reference upper wavelength, thus leading to the first and second reference bands extending at each side of the suspect band, but without overlapping.

In another preferred version of this embodiment, the first reference upper wavelength is at a lower wavelength than the suspect lower wavelength, and the second reference lower wavelength is at a higher wavelength than the suspect upper wavelength, thus leading to the first and second reference bands extending at each side of the suspect band.

In an alternative embodiment, the first and second reference bands are overlapping having at least one common wavelength.

In an especially preferred configuration, the sensor uses the natural radiation, such as IR radiation, from the environment. There is therefore no need for a source of radiation that needs a separate power supply and accordingly has a certain power requirement. IR radiation is generally present everywhere, even when there is no incident sunlight. In principle every body emits a certain amount of thermal radiation. Because it is then possible to do without an IR radiation source, the "measurement range" is also broadened, that is to say it is possible to monitor relatively large areas of a room for the content of the gas in question. This facilitates the monitoring and establishment of a "personal room climate" or the indoor air quality. It is unnecessary first to conduct the air in the room to a sensor where it is passed between the source of IR radiation and the detectors with upstream filters. It is sufficient for the sensor to be arranged at a point in the room where it can, as it were, "survey" the volume of air to be monitored. In that case, the gas sensor can, as it were, detect the averaged gas concentration in a simple way. The sensor therefore determines an average value, which, particularly for the personal room climate, constitutes a substantially better measurement result. Of course, it is also possible to use the sensor to improve the technology of sensors that operate with lamps or other means of lighting. When natural or ambient IR radiation is used, the energy of the light means can be reduced. That results in longer maintenance intervals and a longer service life.

The filters preferably contain $CaF_2$, germanium or silicon. The filter and any other parts of the sensor device where it would make sense, preferably has an anti-reflective coating in order to improve transmission.

BRIEF DESCRIPTION OF THE DRAWINGS

The invention will be described herein below with reference to a preferred exemplary embodiment in conjunction with the drawings.

DETAILED DESCRIPTION OF THE PREFERRED EMBODIMENTS

Figure 1:
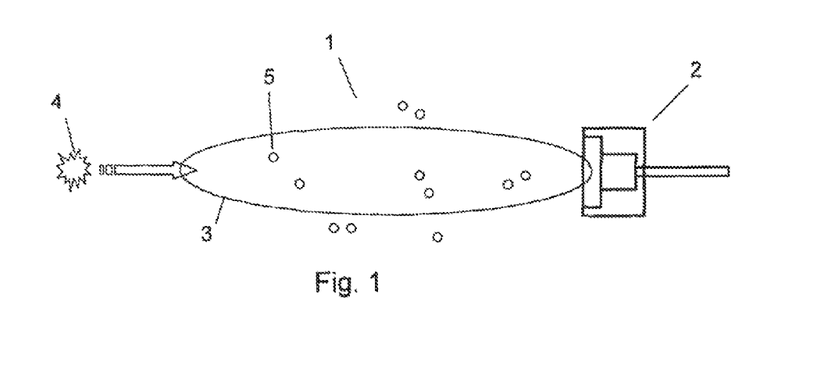
FIG. 1 is a diagrammatic view for explaining the operating principle of the present invention.

FIG. 1 shows a diagrammatic view of a gas sensor (1) for determining for example the $CO_2$ content (carbon dioxide content) in a measurement region (3), where the sensor (1) comprises a detection part (2). The measurement region may be, for example, a room or the portion of a room in which the personal room climate is to be regulated. A sun symbol (4) represents a radiation source, such as for example a natural IR source, passive sources, or any imaginable active source (sunlight, laser, light diodes, controlled hated sources etc.) The sun symbol (4) serves here merely for explanation purposes. The gas sensor (1) also operates in the absence of sunlight, because in principle virtually any body radiates heat and thus generates IR rays.

In the example, a large number of CO2 molecules (5) are present in the measurement region (2), the CO2 molecules (5) being represented herein by small circles. The gas molecules (5) absorb IR rays in a specific spectral range. The greater the concentration of CO2 the lower the energy in a specific spectral range that can be detected in the gas sensor (1).

Figure 5A:
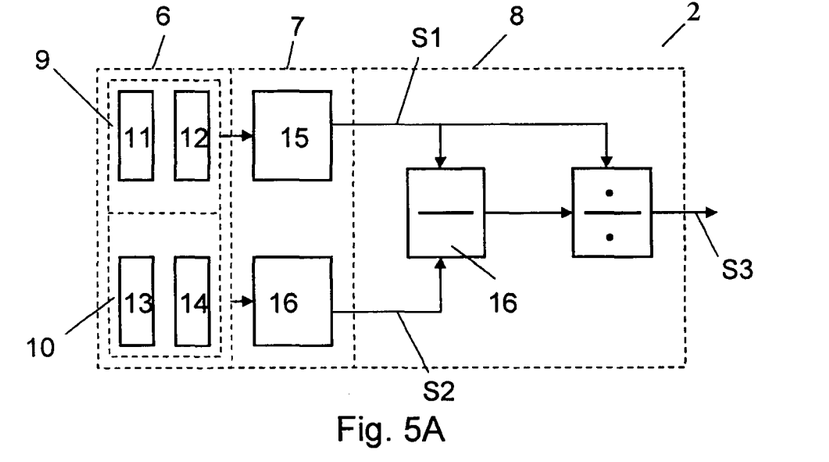
FIGS. 5A-D are block circuit diagrams for explaining different embodiments of the structure of the gas sensor.

FIG. 5A shows, in diagrammatic form, a block circuit diagram for explaining the structure of the simple detecting part (2) of a gas sensor (1). The detecting part (2) has a filter arrangement (6), a detector arrangement (7) and an evaluating device (8). Further details, such as the housing, fixing means or the like, are not shown herein.

Figure 2A:
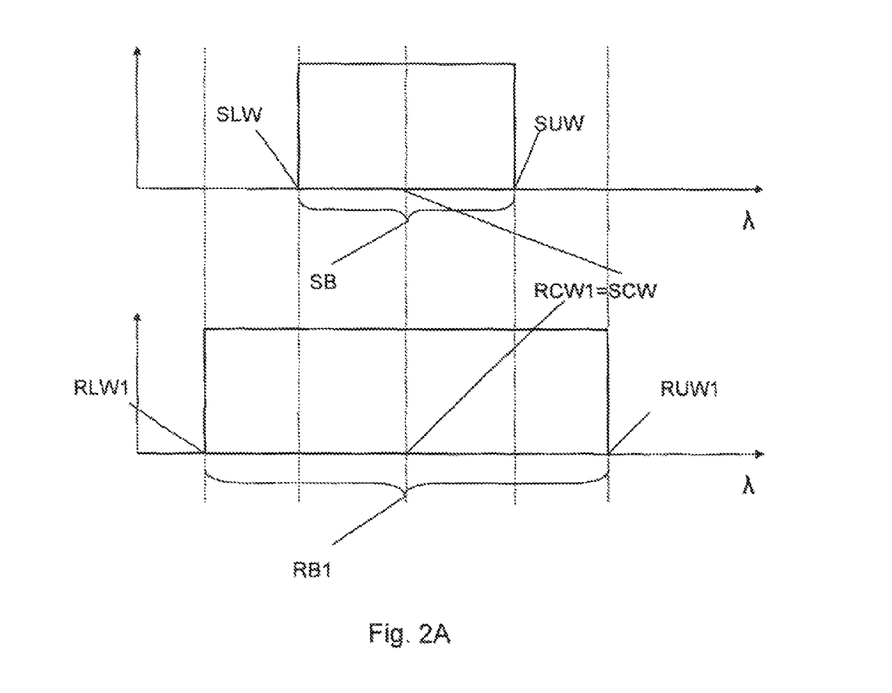
FIGS. 2A-E shows, in diagrammatic form, pass bands of two or three filters.

The shown filter arrangement has a first reference filter (10) and a suspect filter (9), where the two filters (9) and (10) have different pass characteristics, where one embodiment is shown in FIG. 2A. The first reference filter (10) allows passing of wavelengths within the firsts reference band RB1, and the suspect filter (9) allows the passing of wavelengths within the suspect band SB. The embodiment in FIG. 2A shows the first reference band RB1 spanning wider than the suspect band SB, but where the suspect band SB overlaps the first reference band RB1 in such a manner, that the first reference band RB1 comprises the same wavelengths as the suspect band SB. The first reference lower wavelength RLW1 therefore is at a lower wavelength than the suspect lower wavelength SLW, and the first reference upper wavelength RUW1 has a higher wavelength than the suspect upper wavelength SUW. The first reference band RB1 has a first centre wavelength RCW1, and the suspect band has a suspect centre wavelength SCW. The figure shows the two bands having a common centre wavelength RCW1 and SCW.

Figure 2B:
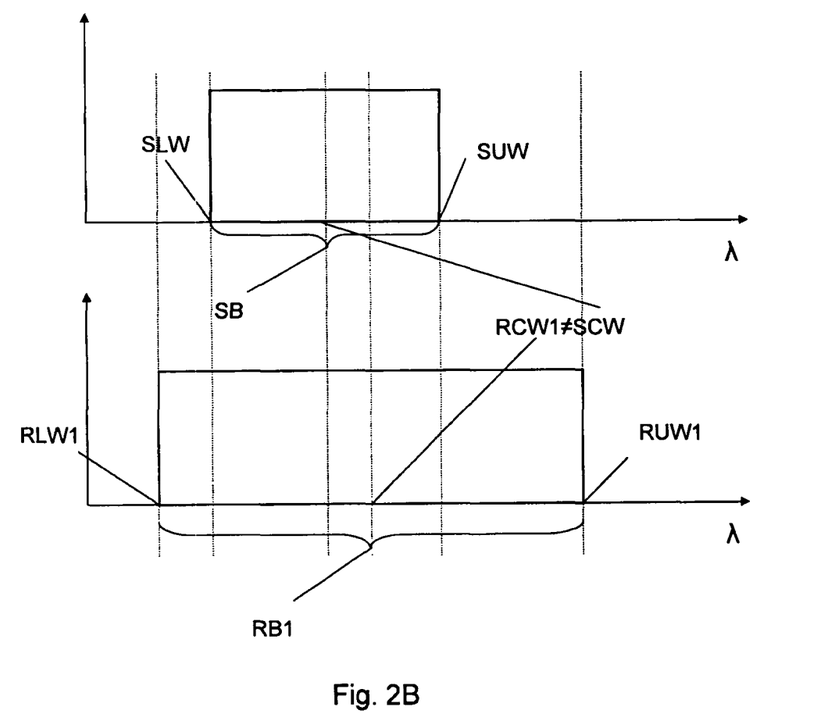

FIG. 2B shows a related embodiment to that shown in FIG. 2A, only where they have dissimilar centre wavelengths SCW and RCW1. For a change in temperature, the relative change in intensity in the suspect and reference band must be equal in order for the temperature dependency to cancel out. When using radiation sources, actively powered or natural the relative change in intensity depends unlinearly on the wavelengths spanned by the bands. Therefore the unmatching centre wavelength can be introduced to improve stability to temperature drift.

Figure 3:
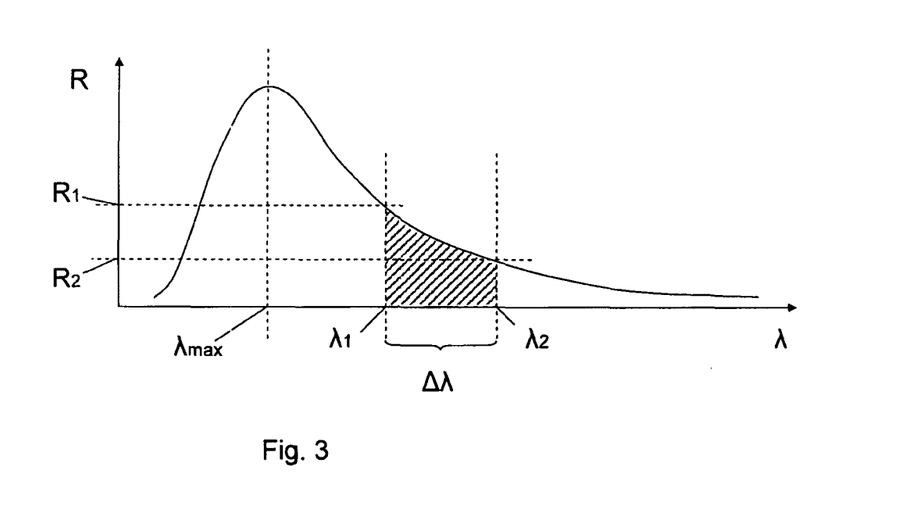
FIG. 3 shows in diagrammatic form a Planck curve and a band with a none-constant radiation intensity.

FIG. 3 illustrates the situation of a source emitting with a spectral distribution represented by a general Planck curve having a maximum radiation at the wavelength $\lambda max$, and having a continuously decreasing radiation for increasing wavelengths above $\lambda max$, so using a band $\Delta\lambda$ between two such wavelengths $\lambda 1$ and $\lambda 2$. The radiation R1 at the lower wavelength $\lambda 1$ being larger than the radiation R2 at the upper wavelength $\lambda 2$.

Therefore, to ensure the same mean values (or averages) of radiation, unmatching centre wavelengths are introduced giving different spans of wavelengths of the reference band(s) below and above the suspect band respectively, where these different spans then compensates the changing radiation intensity.

Figure 2C:
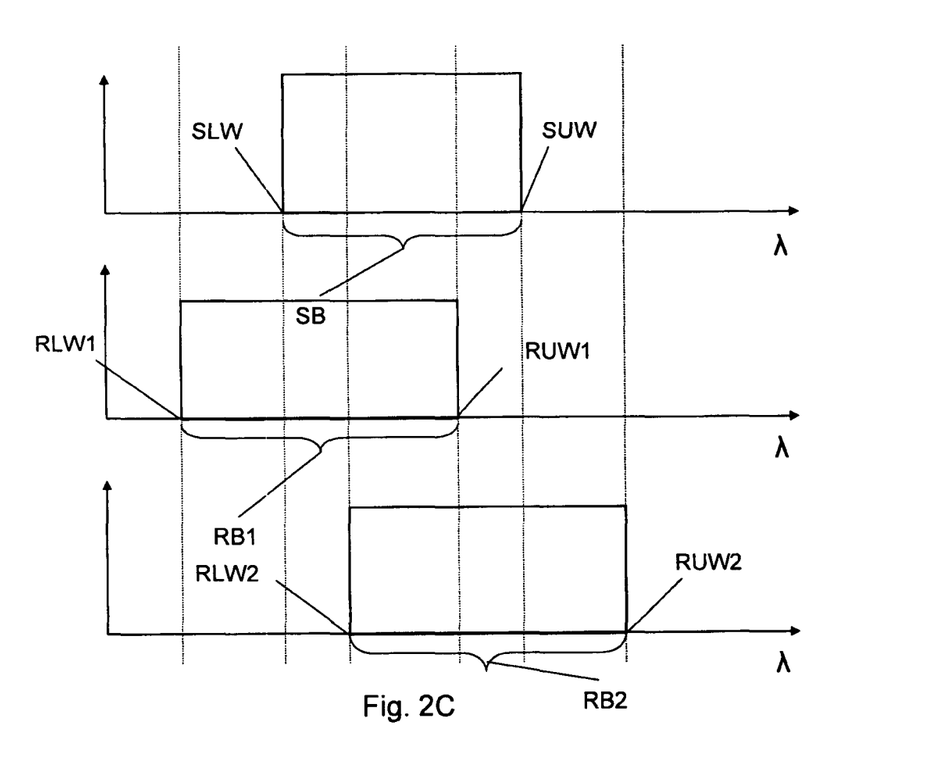

FIG. 2C shows another embodiment where a second reference filter has been introduced into the system spanning over a second reference band RB2 extending from a second reference lower wavelength RLW2 to a second reference upper wavelength RUW2. The shown embodiment further has the suspect band SB only partly overlapping both the first and second reference bands RB1 and RB2 in such a manner, that the suspect lower wavelength SLW is between the first reference lower wavelength RLW1 and the first reference upper wavelength RUW1. The suspect upper wavelength SUW is between the second reference lower wavelength RLW2 and the second reference upper wavelength RUW2. The shown embodiment has the first reference upper wavelength RUW1 being higher than the second reference lower wavelength RLW2, but in other embodiments the first and second reference bands RB1 and RB2 might not overlap, meaning that the first reference upper wavelength RUW1 would be lower or equal to the second reference lower wavelength RLW2.

Figure 2D:
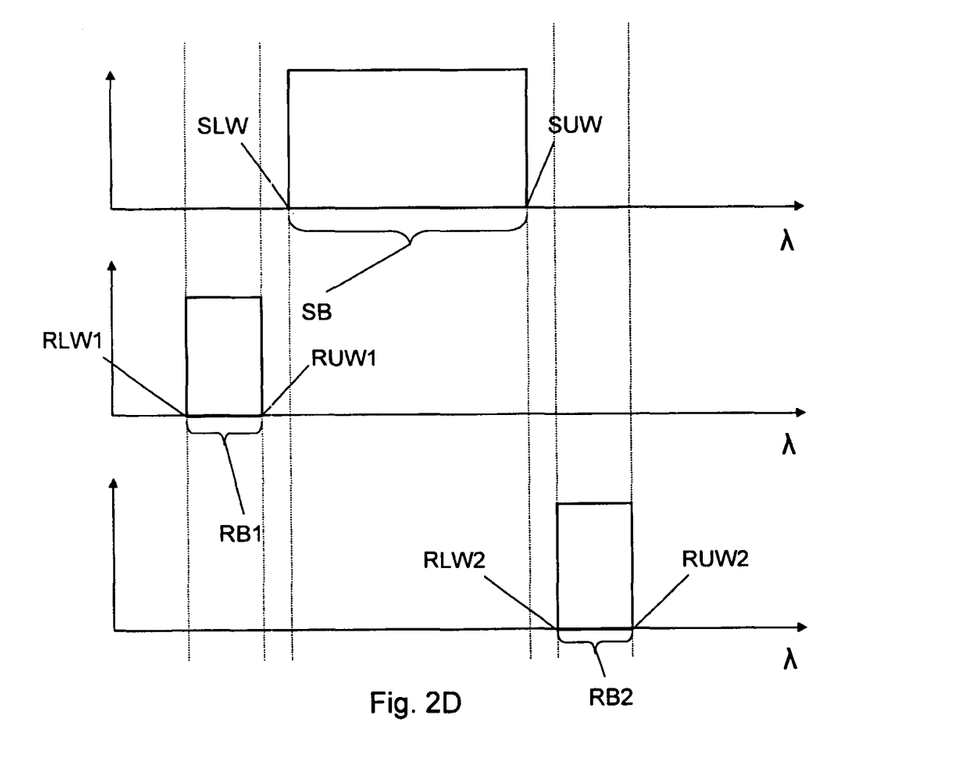
Figure 2E:
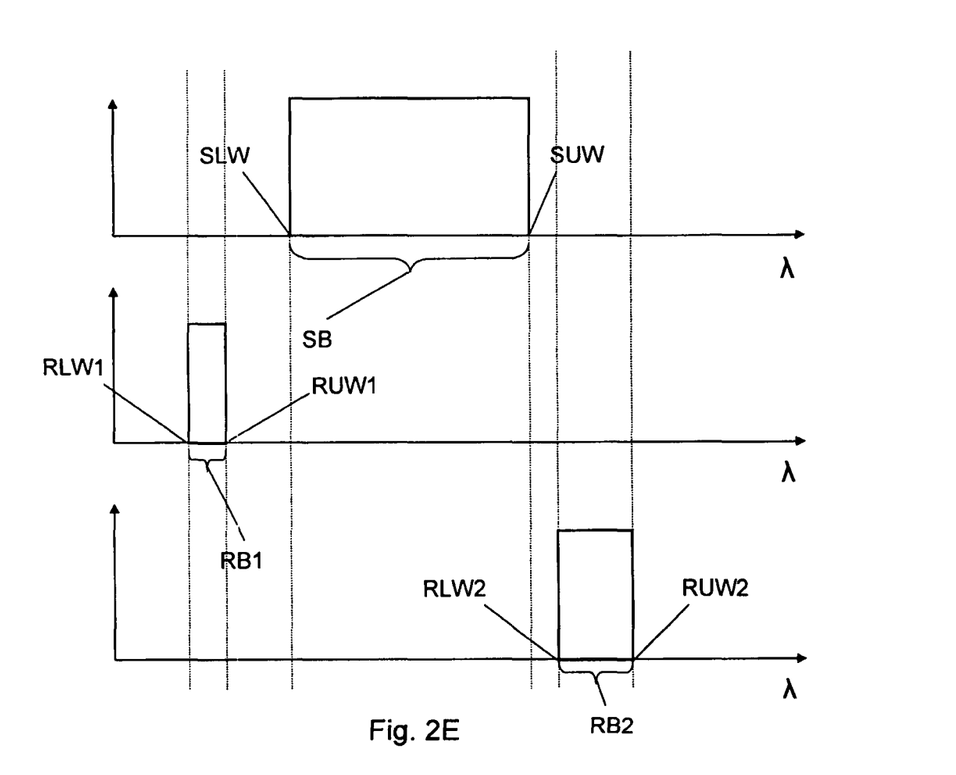

FIG. 2D shows an alternative embodiment with two reference filters (10) and (20), where none of the reference bands RB1 and RB2 at least substantially overlaps the suspect band SB, at least, but extends at each side of it, here meaning, that the first reference upper wavelength RUW1 is not higher than the suspect lower wavelength SLW, but could optionally be the same, and the second reference lower wavelength RLW2 is not lower than the suspect upper wavelength SUW, but could optionally be the same. The figure shows the two reference bands RB1 and RB2 having substantially the same pass range of wavelengths, but as seen in FIG. 2E this may not be the case, the two reference bands RB1 and RB2 might have very different pass ranges of wavelengths.

The relative positions and sizes of the bands depends on a number of factors, such as the tolerances of the edges of the filters, the width of the suspect bandpass, the distribution of the absorption lines of the suspect band, and of any other gasses that might cause cross sensitivities.

In the example of the sensor (1) operating as a $CO_2$ sensor, there is a spectral range λ ($CO_2$) in which IR radiation is absorbed by $CO_2$. That spectral range is located at about from 4.2 to 4.3 µm. Accordingly, the suspect band SB could with advantage have a suspect lower wavelength SLW at about 4.0 µm and a suspect upper wavelength SUW at about 4.5 µm, or with an even more narrow range of the suspect band from 4.1 µm-4.4 µm, or any other band covering the spectral range of $CO_2$ The reference start and upper wavelengths then with advantage could extend about 0.5 µm above and below the suspect lower wavelength SLW and suspect upper wavelength SUW respectively.

Figure 4:
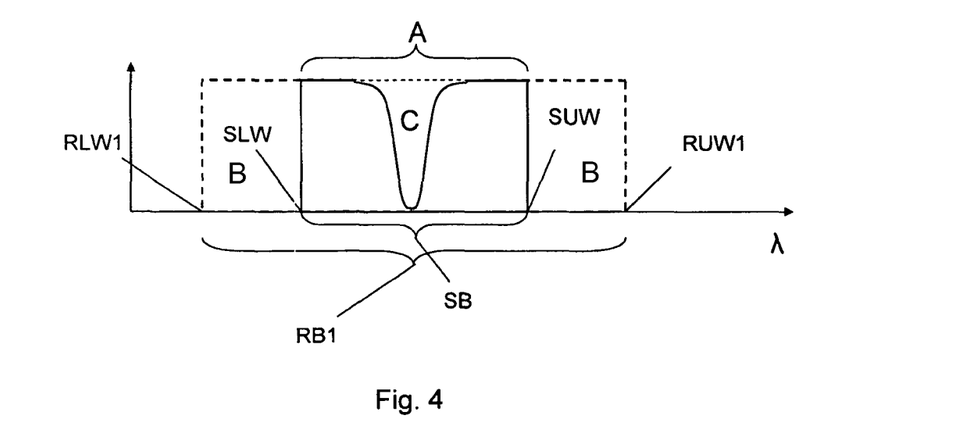
FIG. 4 shows, in diagrammatic form, the amount of energy that can be detected by detectors.

FIG. 4 illustrates a first reference band RB1 and the suspect band SB of the first embodiment of the invention as seen in FIG. 1, where the suspect band has a unreduced energy indicated by reference letter A. That energy is reduced by an amount C which is absorbed by for example $CO_2$. The two sections of the first reference band RB1 extending at each side of the suspect band each has an energy indicated by reference letters B. That energy is virtually constant, because it is not affected by for example $CO_2$.

A thermopile sensor is obtainable, for example, from PerkinElmer Optoelectronics GmbH, D-65199 Wiesbaden, Germany.

Figure 5B:
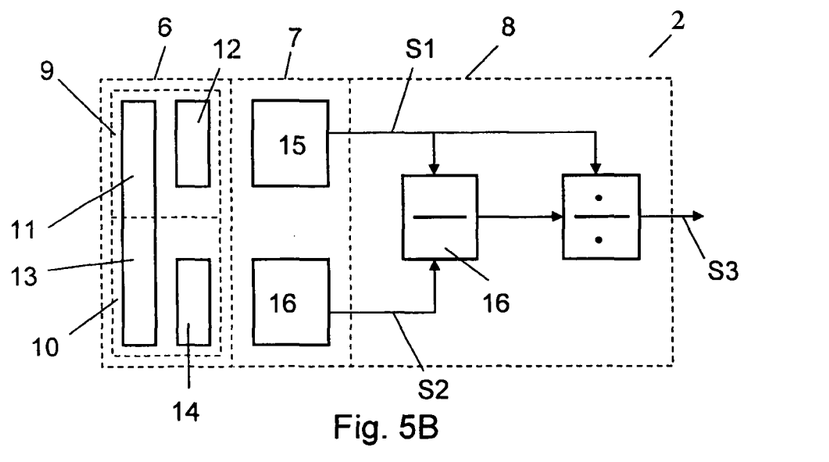

FIG. 5A shows one simple embodiment of a construction of a filter arrangement (6), where the suspect filter (9) comprises two filter elements (11) and (12), the first suspect filter element (11) defining the suspect upper wavelength SUW and having a lower wavelength lower than the suspect lower wavelength SLW. The second suspect filter element (12) defines the suspect lower wavelength SLW and has an upper wavelength substantially higher than the suspect upper wavelength SUW. In the same manner the first reference filter (10) comprises two filter elements (13) and (14) defining the first reference upper wavelength RUW1 and the first reference lower wavelength RLW1 respectively. Depending on the number of filters like (9) and (10) introduced into the system, any number of such constructions of filter elements (11), (12), (13) and (14) may be introduced into the filter arrangement (6). Some filter elements in this and any other embodiment may be common to two or more of the filters when the filters have the same end and/or lower wavelength, this being illustrated in FIG. 5B, where the two 'upper' filter elements (11) and (13) is one common filter element.

Figure 5C:
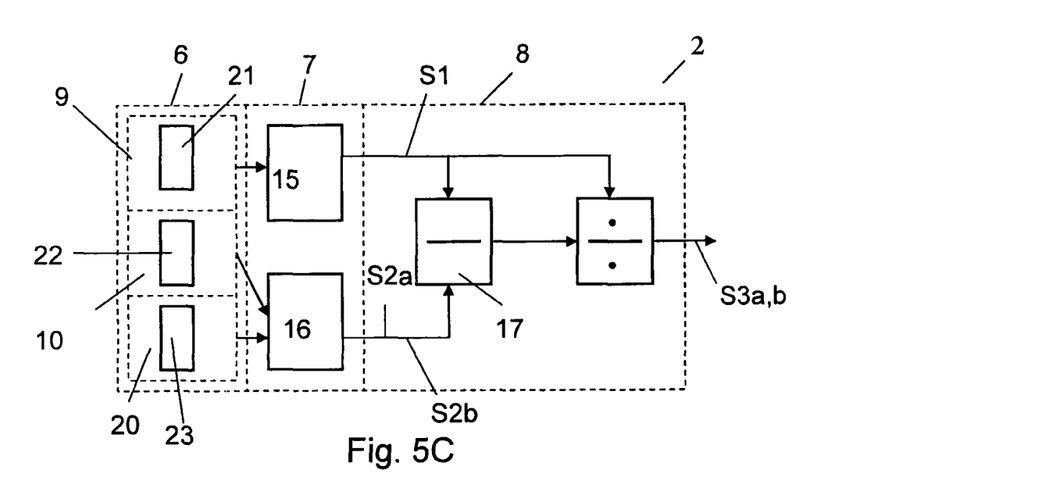

FIG. 5C shows a similar sensor having a extra reference filter, the second reference filter (20), and where each filter only has a single filter element (21, 22, 23) comprising the desired band pass characteristic both for the upper and lower wavelengths, the suspect filter (21) thus both defining both the suspect lower wavelength SLW and upper suspect wavelength SUW. The first reference filter (22) defining both the first reference upper and lower wavelengths RUW1 and RLW1, and the second reference filter (23) defining both the second reference upper and lower wavelengths RUW2 and RLW2. The two filter elopements (22, 23) are in this illustrated embodiment connected to the same detector (16) though in reality what would be done, is to add their signals mathematically after they have been acquired by for example two separated Thermopiles.

Figure 5D:
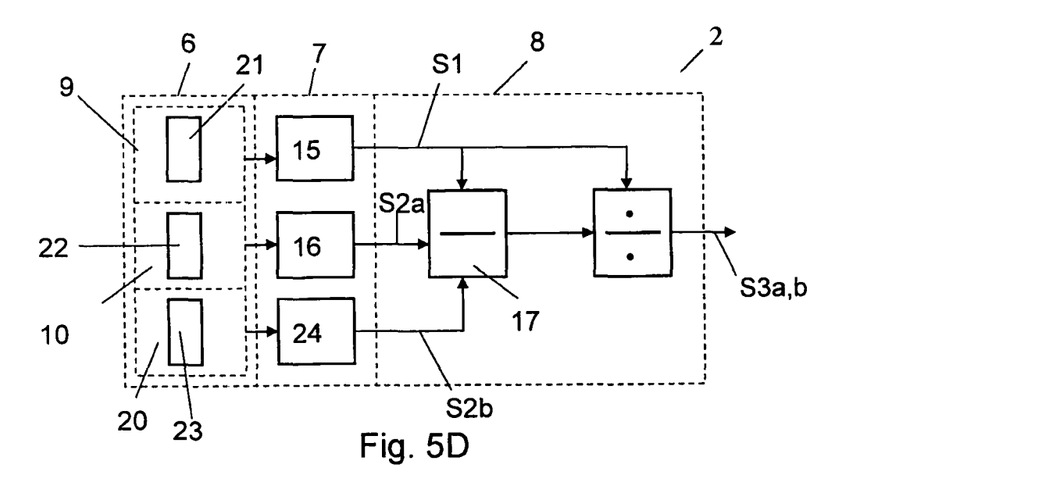

FIG. 5D shows an embodiment related to that of FIG. 5C, only where a third detector (24) is connected to the second reference filter (20).

It shall be noted that any combination, permutation, number and positioning of filter elements (11, 12, 13, 14) as for example disclosed in FIGS. 5A-D would apply to the present invention.

In general the sensor could also be used to measure more than one gas, then just including the needed number of sensors, detectors etc., as it will be known to a craftsman.

The different energies are then detected by the detector arrangement (7). The detector arrangement (7) has a first detector (15) which detects the for example IR radiation which passes through the suspect filter (9), and a second detector (16) which detects the for example IR radiation which passes through the first reference filter (10). The two detectors (15) and (16) can be in the form of thermoelectric elements which are also known as "thermopiles", pyroelectric IR-detectors, or any other kinds of known detectors. In dependence upon the for example IR radiation that occurs, each detector generates a voltage or a current, that is to say an electrical quantity, which is the greater the more IR radiation is incident. Accordingly, the first detector (15) generates a signal S1 and the second detector (16) generates a signal S2.

Because, in a thermopile sensor, usually a temperature measurement is carried out (because the output signal varies with temperature), measurement of the temperature around the sensor has already been incorporated. As it is conceivable that the radiation temperature of the room is also obtainable by means of the sensor, it is possible on the basis of those two measurements simultaneously to obtain directly an operating temperature which can then be used for controlling the room temperature or something quite different.

In connection with IR it is also conceivable that measurement of a movement in the room is directly possible with the sensor, which can then be used, for example, for controlling a ventilating system, which, for example, is activated only in the event of a movement indicating that there is someone in the room. On the basis of various movement measurements it is also conceivable that it would be possible to estimate the number of people in the room, such an estimate also being usable for control purposes, so that the room temperature or the ventilation is controlled/modified in dependence upon the number of people in the room.

The basic sensor of this invention such as the one seen in FIG. 5A operates by the two signals S1, S2 being supplied to the evaluating device (8). Accordingly, this gives $$S1 = a(I_{CO_2 n})$$

$$S2 = a(I_{refn})$$

where $I_{CO_2}$ is the electrical quantity, for example the current or the voltage, containing the information relating to the IR absorption, while $I_{ref}$ is the reference quantity that is not affected by the IR absorption. When the difference between S1 and S2 is formed (the "effective reference" being the part of the reference band which does not include the suspect band), for which purpose a difference former (17) is shown diagrammatically, the following quantity is obtained:

$$S1 - S2 = a(I_{CO_2} - I_{ref})$$

That difference S1−S2 is normalized to the output signal S1 of the first detector (15), so that a signal S3 is obtained.

$$S3 = \frac{S1}{effectiveReference = (S2 - S1)} = \frac{a(I_{CO_2})}{a(I_{Ref})}$$

The sensor of this invention may be used to measure any kinds of gases, such like for example nitrogen, nitric oxides, oxygen or CO, and is not even limited to measure gasses, but may also be used to measure the suspect in other forms like liquids and solids. When changing suspect from $CO_2$, the pass bands would have to be shifted accordingly, for example the absorption band of $H_2O$ is around 2.7 μm.

The sensor of the present invention may further comprise any possible other optical components, for example a sapphire window, that acts as additional band pass filter, reflectors, a collecting device, being a device that gathers or focuses for example IR radiation, for example a collimator, positioned upstream of the sensor, etc.

It is also possible to use such a sensor directly for waste gas monitoring. For that purpose, it is installed in the chimney or exhaust. Particularly in the case of heating systems, combustion can then be controlled with the aid of the output signals of the sensor (or of a plurality of sensors).

This invention is not excluded to the above descriptions and drawings, any permutation of the above descriptions and drawings, including any number and permutations of filters such as suspect filters (9) and reference filters (10, 20), filter elements (21, 22, 23), detectors (15, 16, 24) etc. would also apply to the present invention.

Further, this invention is not excluded to measuring gasses, the sensor may as well be implemented in measuring substances in general being a part of a media, where the media is not excluded to be a gas it self, but could for example be a liquid.

An important aspect of the present invention is especially related to operation temperature conditions that may change (especially the temperature of the light source (3), but also the of the surroundings comprising the gas), either changing over time simply in order to meet a number of different costumer demands in one and the same product. The light source is assumed to have source standard temperature T0, however this may change as the temperature of the surroundings changes, and/or as a delivered power to the light source (3) changes.

An artificial light source will have a source standard temperature T0 since it typically will have a given operational power demand, this being the main influence to the operational temperature. This given operational power demand may then be used to define a source standard temperature T0. The actual operational temperature however may change, such as due to changes in delivered power, due to aging of the light source etc.

Figure 6A:
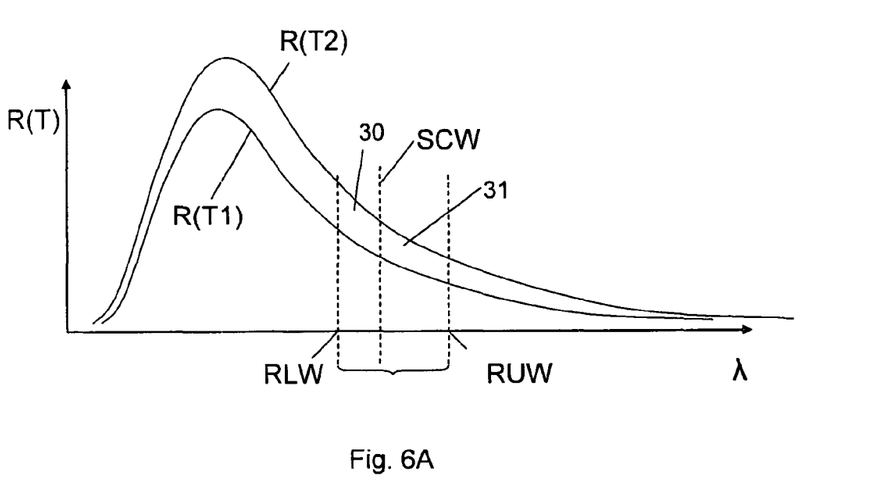
FIGS. 6A-B are temperature relations relevant to the design parameters of the sensor according to the present invention.
Figure 6B:
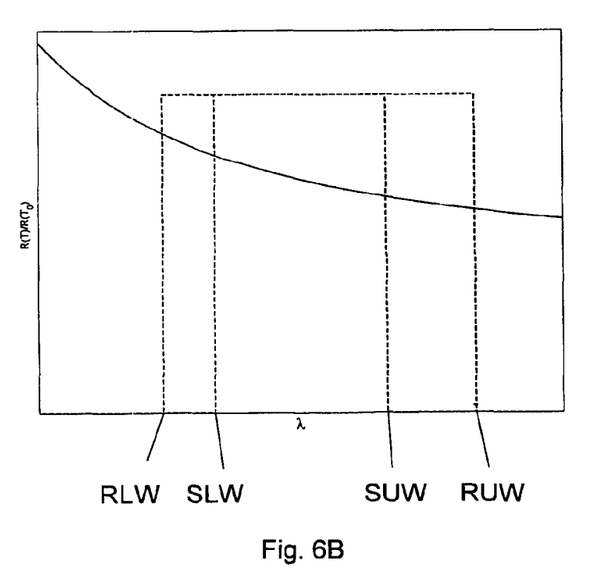

The idea is to shift the (optionally system) reference centre wavelength RCW relative to the suspect centre wavelength SCW so that the temperature derivative of S3(T) at least approximates to a minimum around the source standard temperature T0, meaning dS3(T)/dT is at least approximately minimized around T0. FIGS. 6A and 6B illustrates the situation, where R(T) is the emitted radiation at the temperature T, in order to maximize stability of the system to temperature changes and thereby arising changes in the emitted radiation distribution.

FIG. 6A illustrates the emitted radiation curves at two different temperatures T1 and T2, and FIG. 6B illustrates the relation of these two curves R(T1) and R(T2) in the wave band specified by the reference system lower wavelength RLW and reference system upper wavelength RUW.

By choosing the shift of the reference centre wavelength RCW relative to the suspect centre wavelength SCW such stability may be obtained. This shift may be found by minimizing dS3(T)/dT around T0.

The improvement in stability is especially important for lower source temperatures, like for passive sources at room temperature or chimney temperatures (200-300 degrees Celsius). This is because the lower the source temperature, the greater the sensitivity towards changes in source temperatures. In the same manner, gas measurements in the lower wavelength range (<3 micro meters) are more affected by changes in source temperature than measurements at longer wavelength ranges. Hence the improvement potential greater for the lower wavelengths range as for lower source temperatures, albeit, improvements can be achieved for all source temperature and wavelength ranges.

Although the invention above has been described in connection with preferred embodiments of the invention, it will be evident for a person skilled in the art that several modifications are conceivable without departing from the invention as defined by the following claims.

What is claimed is:

1. A sensor having,
a filter arrangement,
a detector arrangement downstream from the filter arrangement, and
an evaluating device which is connected to the detector arrangement,
wherein the filter arrangement has a suspect filter configured to pass through radiation with wavelengths within a suspect band, and the filter arrangement has a reference filter system with at least one reference filter, each reference filter of the at least one reference filter configured to pass through radiation with wavelengths at least within a reference band and where a reference system band is the combined reference bands of all the reference filters of the at least one reference filter,
wherein the detector arrangement has at least two detectors,
wherein a first detector of the at least two detectors is associated with the suspect filter and is configured to provide a first output signal to the evaluating device and a second detector of the at least two detectors is associated with one of the reference filters of the at least one reference filter and is configured to provide a second output signal to the evaluating device,
wherein the reference system band is distributed on both sides of the suspect band,
wherein the evaluating device is configured to normalize a difference between the first and second output signals to the output signal of the first detector to obtain a signal S3 by dividing the difference between the first and second output signals by the first output signal of the first detector, and
wherein the reference band of the at least one reference filter has a centre wave length shifted relative to a suspect centre wave length of the suspect band so that a temperature derivative dS3(T)/dT of S3 is minimized around a chosen temperature.

2. The sensor according to claim 1, wherein the suspect band at least partly overlaps the reference system band.

3. The sensor according to claim 2, wherein the reference system comprises a single filter, the single filter having a first reference band.

4. The sensor according to claim 3, wherein the suspect band and the first reference band have a different centre wavelength.

5. The sensor according to claim 3, wherein all the wavelengths of the suspect band also are present in the first reference band.

6. The sensor according to claim 1, wherein the sensor comprises any number of suspects filters for measuring any number of different gasses.

7. The sensor according to claim 1, wherein the chosen temperature is a source standard temperature T0.

8. The sensor according to claim 1, wherein the sensor comprises a light source having a source standard temperature T0.

9. A sensor system comprising,
a light source having a source standard temperature T0,
a filter arrangement,
a detector arrangement downstream of the filter arrangement, and
an evaluating device which is connected to the detector arrangement,
wherein the filter arrangement has a suspect filter configured to pass through radiation with wavelengths within a suspect band, and the filter arrangement has a reference filter system with at least one reference filter, each reference filter of the at least one reference filter configured to pass through radiation with wavelengths at least within a reference band and where a reference system band is the combined reference bands of all the reference filters of the at least one reference filter,
wherein the detector arrangement has at least two detectors,
wherein a first detector of the at least two detectors is associated with the suspect filter and is configured to provide a first output signal to the evaluating device and a second detector of the at least two detectors is associated with one of the reference filters of the at least one reference filter and is configured to provide a second output signal to the evaluating device,
wherein the evaluating device is configured to normalize a difference between the first and second output signals to the output signal of the first detector to obtain a signal S3 by dividing the difference between the first and second output signals by the first output signal of the first detector, and
wherein the reference system band is distributed on both sides of the suspect band such that a temperature derivative $dS3(T)/dT$ of S3 at least substantially forms a minimum around a source standard temperature T0.

10. The sensor system according to claim 9, wherein the reference band of at least one reference filter has a centre wave length shifted relative to a suspect centre wave length of the suspect band so that $dS3(T)/dT$ at least substantially forms said minimum around T0.

* * * * *